United States Patent [19]
Rathod

[11] Patent Number: 6,159,953
[45] Date of Patent: Dec. 12, 2000

[54] ANTI-MALARIAL COMPOSITION AND METHOD OF USE

[75] Inventor: Pradipsinh K Rathod, Wheaton, Md.

[73] Assignee: Catholic University of America, Washington, D.C.

[21] Appl. No.: 07/851,103

[22] Filed: Mar. 16, 1992

Related U.S. Application Data

[63] Continuation of application No. 07/369,472, Jun. 21, 1989, abandoned.

[51] Int. Cl.[7] .................................................. A61K 31/715
[52] U.S. Cl. .............................. 514/49; 514/50; 514/261; 514/269; 514/885; 536/23.1
[58] Field of Search ........................ 536/23, 23.1; 514/49, 514/50, 261, 269, 885

[56] References Cited

U.S. PATENT DOCUMENTS

| | | | |
|---|---|---|---|
| 3,775,397 | 11/1973 | Etzold et al. | 536/23 |
| 4,873,228 | 10/1989 | Schmalzl et al. | 514/49 |

OTHER PUBLICATIONS

Klubes, P., et al., Cancer Res. 43:3182 (1983).
Hammond, D.J., Molec. Biochem. Pharmacol. 14:97 (1985).
Rathod, P.K., et al., J. Cellular Biochem., Suppl. 13E, Abs. 0555 (1989).
McCormick, G.J., et al., Antimicrob. Agents and Chemotherap., 6:16 (1974).
Ullman, B., et al., Molec. Pharm., 15:357 (1979).
Martin, D.S., et al., Cancer Res. 42:3964 (1982).
Jerry L. Adams, et al., "CIS–4–Carboxy– 6–(Mercaptomethyl)–3,4,5,6–Tetrahydropyrimidin–2(1H)–One, A Potent Inhibitor of Mammalian Dihydroorotase" J. Med. Chem. (1988) pp. 1355–1359.

*Primary Examiner*—James O. Wilson
*Attorney, Agent, or Firm*—Pillsbury Madison & Sutro LLP

[57] ABSTRACT

Anti-malarial compositions for prophylactic or therapeutic treatment of vertebrates exposed to malaria parasites are disclosed. These compositions comprise one or more pyrimidine analogue inhibitors of nucleic acid biosynthesis, e.g., 5-fluoro-orotic acid, alone or together with one or more "rescue" compounds, e.g., a normal pyrimidine base or nucleoside that can be used by the host vertebrate, but not by malaria-causing parasites, for nucleic acid biosynthesis. Also claimed are methods of prophylactic and therapeutic use of these compositions.

2 Claims, 10 Drawing Sheets

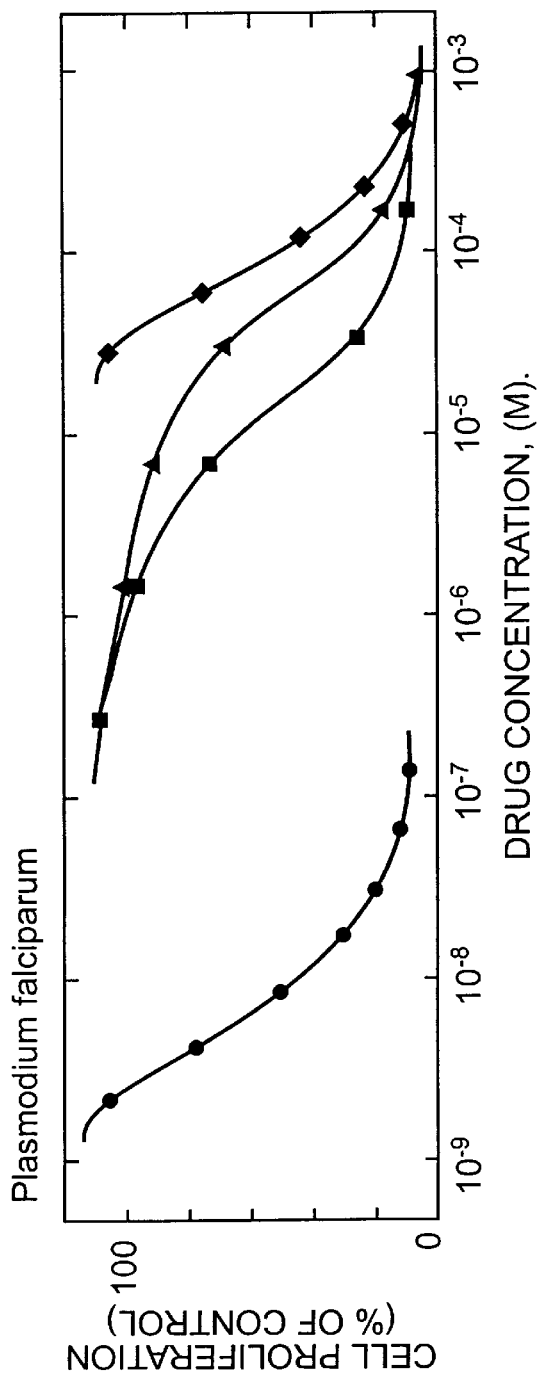
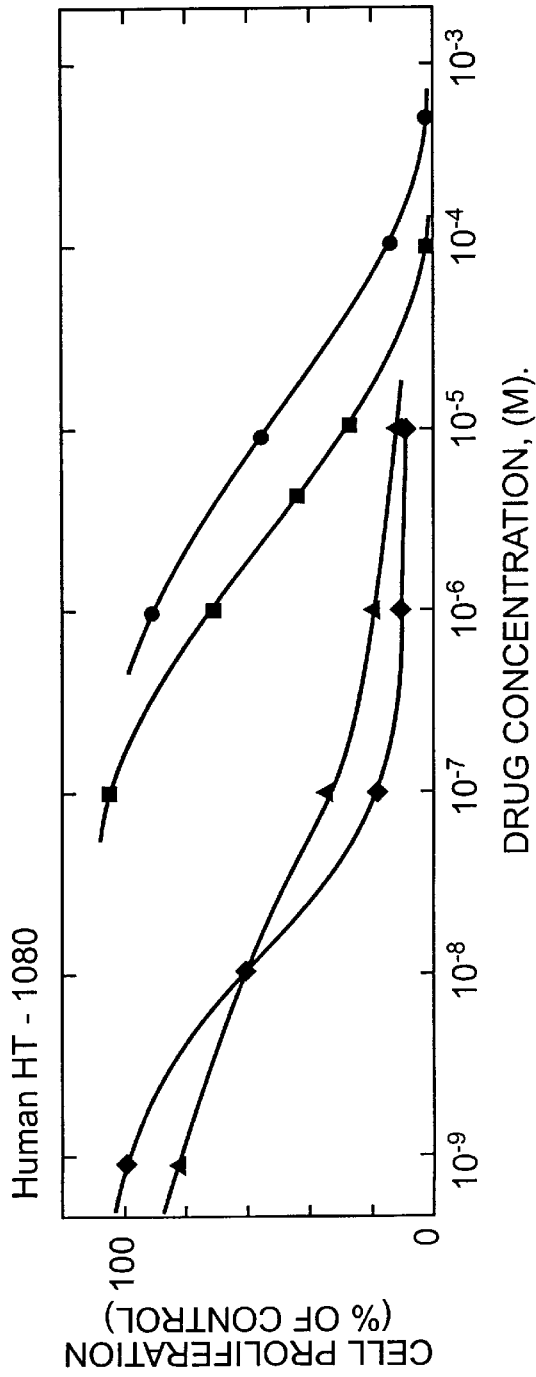
FIG. 1A
FIG. 1B

ANTI-MALARIAL COMPOSITION AND METHOD OF USE

This is a continuation of application Ser. No. 07/369,472, filed on Jun. 21, 1989, which is now abandoned.

BACKGROUND OF THE INVENTION

1. Field of the Invention

This invention relates to compositions useful in the treatment of humans and other vertebrates infected with malaria parasites. More particularly, this invention relates to prophylactic and therapeutic compositions containing as active ingredients one or more substances that are toxic to the malaria-causing parasite alone or in combination with one or more substances that rescue the host vertebrate from the toxic effects of the anti-parasitic compositions. This invention also relates to the use of the aforementioned compositions for the prophylactic and therapeutic treatment of malaria in animal and human patients.

2. Description of Related Art

Malaria is a debilitating and often fatal disease caused by protozoans of the genus Plasmodium. According to World Health Organization estimates about 2.2 billion people live in areas in which malaria is still endemic, but control measures have decreased the level of toxicity; however, over 350 million people live in areas of the world in which malaria is highly endemic and no special antimalarial measures are being applied. "Science at Work: Special Programme for Research and Training in Tropical Diseases", UNDP/World Bank/WHO, Geneva, 2d ed., 1986.

Currently, quinine-based drugs, particularly chloroquine, are the mainstay of anti-malarial chemoprophylaxis, particularly for those species for Plasmodium that are sensitive to this drug, i.e., *P. knowlesi, P. vivax, P. ovale, P. malariae, P. yoelii* and cloroquine-sensitive *P. falciparum* [Herwaldt, B. L., et al., *Antimicrob. Agents Chemotherap.*, 32:953 (1988); Krogstad, D. J., et al., Id., p. 957]. There are several important problems attendant upon the use of chloroquine as an anti-malarial. Although oral chloroquine typically is well-tolerated, some patients experience serious side effects. In addition, the safety of parenteral chloroquine has been questioned because it may cause cardiac arrhythmia and sudden death in children. Krogstad, et al. 1988 at 957. Further, *P. falciparum* strains resistant to chloroquine and other traditional drugs are known in at least 40 tropical and subtropical countries [Payne, D., *Parisitol. Today*, 3:241–5 (1987); Wyler, D. J., *N. Eng. J. Med.*, 308, 875 (1983)]. In areas with chloroquine-resistant *P. falciparum,* combination therapies have been recommended (chloroquine plus pyrimethamine-plus-sulfodoxine), but the latter components are known to cause severe, even fatal, reactions [Herwaldt et al. 1988, at 953]. Furthermore, correlations between the in vitro suspectibility of parasites to chloroquine, mefloquine or other anti-malarial agents and clinical effectiveness are known to be very imprecise, and are more qualitative than quantitative [Herwaldt et al. 1988, at 953]. The future of malarial chemotherapy is particularly alarming in view of parasite strains that display cross-resistance to several structurally unrelated drugs [Hubbert, T. E., et al., 35th Ann. Mtg. Amer. Soc. Trop. Med. Hyg., Denver, Colo., 1986; Webster, H. K., et al., *Am. J. Trop. Med. Hyg.*, 34:228–35 (1985)].

Thus, it is important to develop novel antimalarial drugs, particularly those that are effective against strains of malaria-causing parasites that display single or multiple drug resistance.

The erythrocytic phase of the life cycle of *P. falciparum* is associated with clinical symptoms of malaria. During this 48 hour asexual cycle, each parasite inside a red blood cell generates 6 to 24 offspring that burst out and individually invade fresh erythrocytes. The exponential increase in parasites requires a steady supply of purine and pyrimidine nucleotides for the DNA and RNA synthesis necessary for their growth. Malarial parasites are able to use the rich pool of adenine nucleotides inside the erythrocytes to obtain their supply of purines, but these parasites, lacking the "salvage" pathway, cannot use preformed pyrimidines and, thus, must synthesize them de novo [Sherman, I. W., et al., *Microbiol. Rev.*, 43:453–96 (1979); Reyes, P., et al., *Mol. Biochem. Parasitol.*, 5:275–90 (1982); Rathod, P. K., et al., *J. Biol. Chem.*, 258:2852–5 (1983)]. In contrast, mammalian cells are able to utilize preformed pyrimidine bases and nucleosides by salvage pathways [Jones, M. E., *Ann. Rev. Biochem.*, 49:253–79; Moyer, J. D., et al., *J. Biol. Chem.*, 260:2812–18 (1985)].

These distinctions in pyrimidine metabolisms between malaria parasites and the cells of host mammals have led to the present discovery of anti-malarial prophylactic and therapeutic compositions that are lethal to such parasites, but not toxic to the host vertebrates harboring these parasites.

SUMMARY OF THE INVENTION

This invention provides compositions that inhibit the growth of malarial parasites in parasite-infected vertebrates, but which are without deleterious effects on the host vertebrate.

It has now been discovered that certain pyrimidine analogues that inhibit de novo pyrimidine metabolism and are toxic to vertebrate cells can be used to inhibit the growth of malarial parasites and in parasite-infected vertebrates in vivo.

It has also been discovered that the toxic effects of the aforementioned pyrimidine analogues on the cells of malaria parasite-infected vertebrates can be alleviated, if necessary, by the administration to intact vertebrates in vivo, of "rescue" compounds, e.g., normal pyrimidine bases or nucleosides that support the "salvage" pathway of pyrimidine metabolism. Thus the vertebrate can be "rescued" from both the effects of the parasites and the potentially toxic effects of the pyrimidine analogues used to prevent parasite proliferation.

It is, therefore, an object of this invention to provide prophylactic and therapeutic compositions for vertebrates exposed to malaria parasites and malaria parasite-infected vertebrates. These compositions comprise one or more pyrimidine analogues that block de novo pyrimidine, and thus nucleic acid, biosynthesis, alone or together with a "rescue" compound, e.g., one or more normal pyrimidine bases or nucleosides that by-pass the effects of the blocked de novo pyrimidine biosynthesis pathway in the host vertebrate, but not in the parasites.

A further object of this invention is to provide pyrimidine analogue compositions that are toxic to malaria parasites in vivo.

Yet another object of this invention is to provide pyrimidine bases and nucleosides that are capable of rescuing the malaria parasite-infected vertebrate, but not the parasites themselves, from the toxic effects of the pyrimidine analogues.

It is still another object of the invention to provide methods of treatment of malaria parasite-infected vertebrates and prophylactic methods for vertebrates exposed to malaria parasites using the aforementioned compositions in a pharmaceutically-acceptable vehicle.

These and other objects, as well as the nature, scope and utilization of this invention, will become readily apparent to those skilled in the art from the following description, the drawings and the appended claims.

BRIEF DESCRIPTION OF THE DRAWINGS

FIG. 1 illustrates inhibition of proliferation of (A) cultured *P. falciparum* and (B) human HT-1080 cells by fluoropyrimidines. In the antimalarial experiment with parasites, incorporation of radioactivity from [G-$^3$H]-hypoxanthine into nucleic acids served as a measure of parasite proliferation. Control wells incorporated 11,200 cpm of tritium from labelled hypoxanthine into precipitable nucleic acids. Each data point represents an average of two determinations. In the study of toxicity to human cells, proliferation of cells was determined directly by measuring the number of viable cells per well. Control wells showed a net increase of 350,000 cells during the 48 hour incubation. Each data point represents an average of two determinations. 5-fluoroorotate (●), 5-fluorouracil (■), 5-fluorouridine (▲), and 5-fluoro-2'-deoxyuridine (♦).

DETAILED DESCRIPTION OF THE INVENTION

Figure 2:
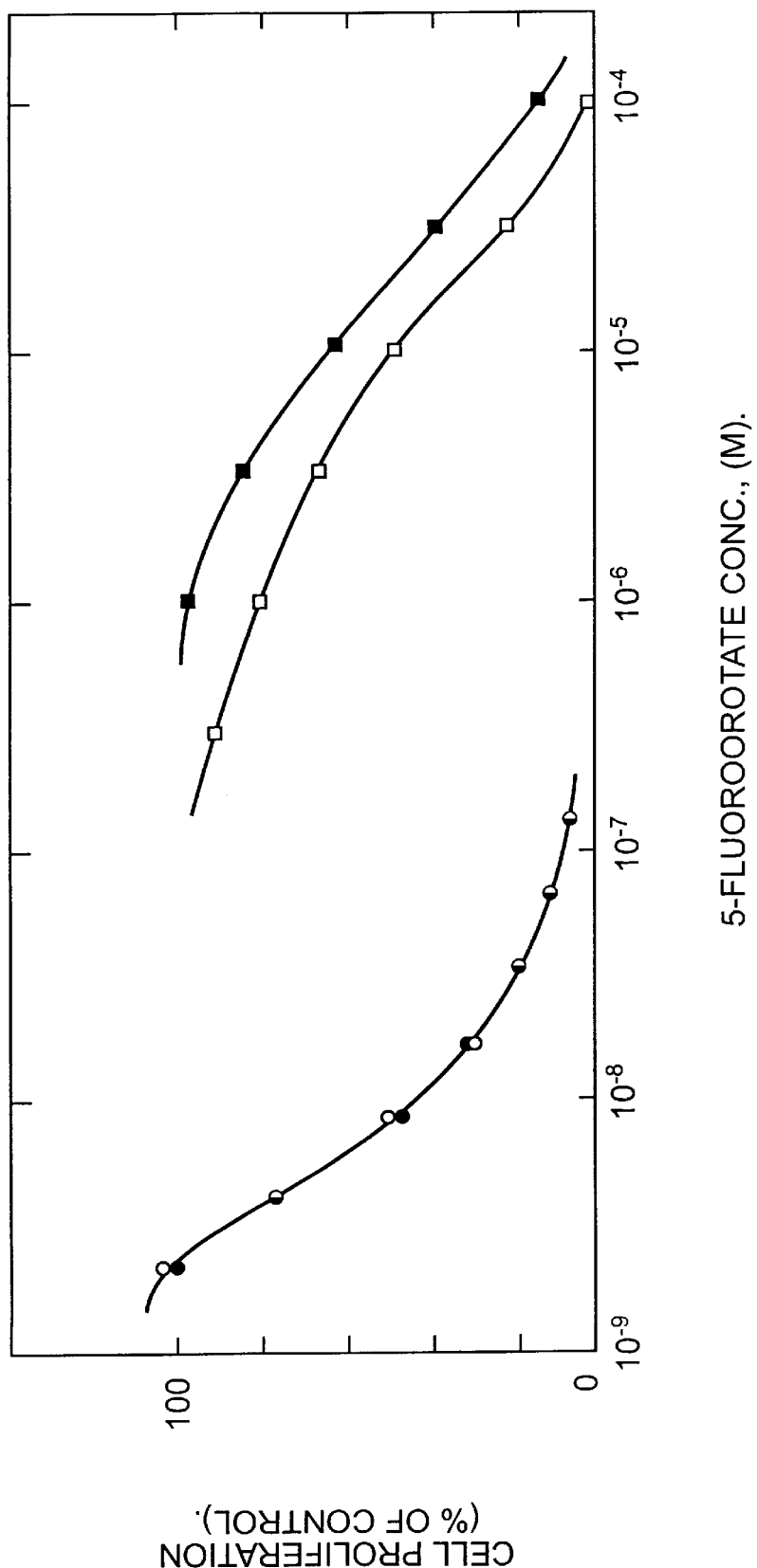
FIG. 2 illustrates the effects of uridine on the cytotoxicity of 5-fluoro-orotate. As in FIG. 1, cells were grown for 48 hours with varying concentrations of 5-fluoroorotate. Indochina clone W-2 of *P. falciparum* without uridine (○) and with 1 mM uridine (●); Human HT-1080 cells without uridine (□) and with 1 mM uridine (■). Half shaded symbols represent overlapping data points.

The anti-malarial prophylactic and therapeutic compositions of this invention contain, inter alia, one or more pyrimidine analogues known to inhibit pyrimidine, and therefore nucleic acid, biosynthesis, and which as a result, are lethal to malaria-causing Plasmodium parasites.

Such pyrimidine analogues, at certain dosage levels, can also be toxic to host vertebrates harboring the malaria parasite. Therefore, the anti-malarial compositions of this invention can also contain, if necessary, a compound that will "rescue" the host vertebrate from the toxic effects of the pyrimidine analogues. Included among such "rescue" compounds are normal pyrimidine bases or nucleosides. Such normal pyrimidine bases or nucleosides rescue the host vertebrate, but not the parasites, from toxic effects of pyrimidine analogues by virtue of the fact that vertebrates, but not Plasmodium parasites, possess the "salvage" pathway that allows the utilization of preformed pyrimidine bases or nucleosides. By this means, the host, but not malaria parasites, can be caused to by-pass the toxic affects of the blockade of pyrimidine biosynthetic pathways caused by the administration of pyrimidine analogues.

The de novo pathway for the biosynthesis of the pyrimidine nucleotides required for RNA synthesis in both vertebrates and malaria parasites is shown below:

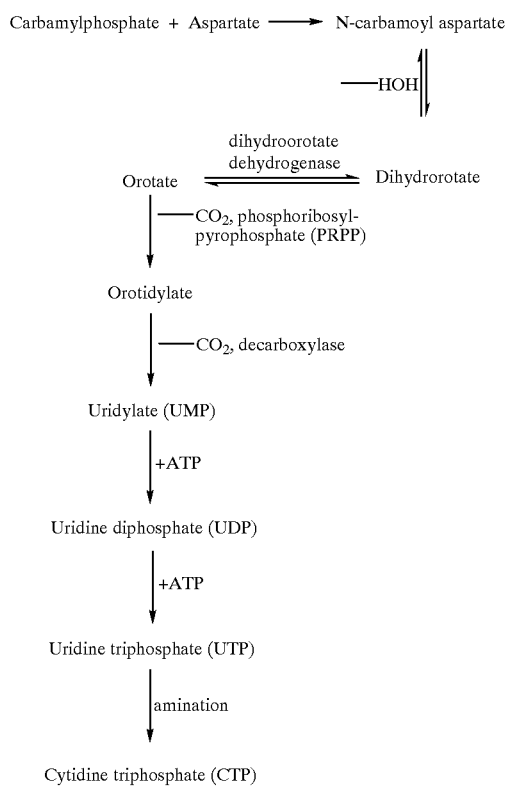

As noted above, vertebrates, but not malaria parasites, are capable of producing pyrimidine nucleotides from pyrimidine bases and nucleosides by "salvage" pathways. These pathways include: (a) generation of uridylate (UMP) from uridine plus ATP by uridine-cytidine kinase; (b) production of UMP from uracil plus PRPP by uracil phosphoribosyl transferase; (c) synthesis of uridine from uracil plus ribose-1-P by uridine phosphorylase, (d) deamination of cytidine by cytidine deaminase to produce uridine; (e) generation of CMP from cytidine plus ATP by uridine-cytidine kinase; and (f) generation of CTP from cytidine-5'-monophosphate (CMP) by consecutive transfers of phosphate from ATP, with the intermediate formation of cytidine-5'-diphosphate, in reactions catalyzed by cytidylate kinase and nucleoside diphosphate kinase.

As noted above, Plasmodium parasites do not have a salvage pathway, and consequently cannot use preformed pyrimidine bases or nucleosides for RNA syntheses. Such parasites must use the de novo pathway shown above. Thus, it has been discovered that an effective inhibitor of de novo pyrimidine biosynthesis also inhibits the proliferation of Plasmodium parasites. Malarial parasites utilize orotate more efficiently than uracil and uridine for RNA synthesis. Thus, it has been discovered that orotate analogues are particularly suitable for blocking de novo synthesis of pyrimidine nucleotides from orotate in malarial parasites. Suitable orotic acid analogues include 5-fluoro-orotic acid, 5-nitro-orotic acid, 5-bromo-orotic acid, 5-thio-orotic acid, 5-diazo-orotic acid, 5-aza-orotic acid, 5-cyano-orotic acid, 5-ethynyl-orotic acid, 5-mono, di-, and tri-fluoromethyl-orotic acid, 5-hydroxymethyl-orotic acid, 5-thiomethyl-orotic acid, esters and amides of the aforementioned orotic acid analogues, O-acyl and N-acyl derivatives of orotic acid and the aforementioned orotic acid analogues, and their cis, and trans-5,6-dihydro counterparts. 5-Fluoro-orotic acid and its trans-5,6-dihydro counterparts are particularly preferred. Throughout the specification, the terms "orotate" or "orotic acid" will be used interchangeably; the former represents the salt form of the latter that will be present at physiological pH values, i.e., above about 7.4.

In vertebrate cells, and likely in parasite cells, 5-fluoro-orotate is metabolized to 5-fluoro-uridylate and thence to 5-fluoro-cytidylate. 5-Fluoro-uridylate and most of its metabolic products accumulate in target cells because they are phosphate esters that cannot diffuse out of the cell [Wilkinson, D. S., et al., Cancer Res., 36:4032 (1976)]. Further transformation of 5-fluoro-uridylate is analogous to the metabolism of uridylate, with one major exception: 5-fluoro-2'-deoxy-uridylate is a potent enzyme-activated inhibitor of thymidylate synthesis, and thus an inhibitor of DNA synthesis [Heidelberger, C., et al., Adv. Enzymol., 54:57 (1983)]. While this is a very likely explanation for the toxic effects of 5-fluoro-orotate, it is not the only possibility; 5-fluoro-pyrimidine nucleoside triphosphates, i.e., 5-F-UTP and 5-F-CTP, are incorporated into RNA, producing a non-functional analogue of RNA [Glazer, R., et al., Mol. Pharmacol., 17:279 (1980)], and to a lesser extent are also incorporated into DNA, producing a non-functional DNA species [Kufe, D., et al., J. Biol. Chem., 256:8885 (1981)].

Trans-5-fluoro-5,6-dihydroorotate (tFDHO) will interact with dihydroorotate dehydrogenase and be converted to 5-fluoro-orotate inside the parasite. In addition, tFDHO will be hydrolyzed by dihydroorotase to the fluorinated analogue of carbamyl-aspartate; this analogue will be converted to threo-3-fluoro-aspartate, an amino acid analogue itself known to have cytotoxic actions [Stern, A. M., et al., J. Med. Chem., 25:544 (1982)]. As malarial parasites do not effectively incorporate exogenous aspartate [Sherman, I. W., Microbiol. Rev., 43:453 (1979)], parasites will remain vulnerable to tFDHO.

tFDHO is not available commercially. However, it can be synthesized by stereospecific enzymatic reduction of 5-fluoro-orotate using Z. oroticum dihydroorotate dehydrogenase and NADH, 5 followed by purification by anion exchange chromatography. A 500 MHz proton NMR of a pure sample prepared by the inventor using this method was in complete agreement with the expected structure. The 5-H resonates at 5.43 ppm and the 6-H at 4.53 ppm. The 5-H to F geminal-coupling constant is 47 Hz. The 6-H to F vicinal coupling constant is 13 Hz. Treatment of tFDHO with bacterial dehydroorotate dehydrogenase and NAD⁺ results in reversion to 5-fluoro-orotate:

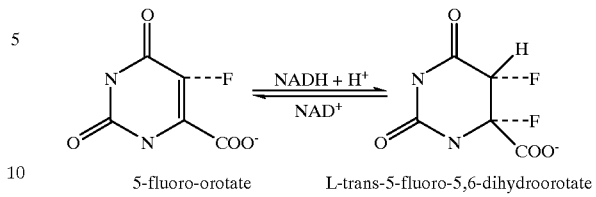

5-fluoro-orotate      L-trans-5-fluoro-5,6-dihydroorotate

The interconversions between these two analogues can be followed on a Pharmacia FPLC system using a mono-Q-column.

The prophylactic and therapeutic compositions of this invention can also contain, as discussed above, a compound or compounds such as one or more normal pyrimidine bases or nucleosides that selectively "rescue" the host vertebrate, but not the malaria parasite, from the toxic effects of the aforementioned orotate analogues by saturating the pool of pyrimidine nucleotides with non-substituted (e.g., non-fluorinated) metabolites. Suitable pyrimidine bases or nucleosides include uracil, uridine, cytosine, cytidine, deoxycytidine, thymine, and deoxythymidine. Uridine is particularly preferred.

The pyrimidine bases and nucleosides, and pyrimidine analogues other than tFDHO, that can be used in practicing this invention, are available commercially (Sigma Chemical Co., St. Louis, Mo. 63178).

It is not always necessary to rescue the host vertebrate from the toxic effects of a pyrimidine analogue. For example, mild cases of malaria parasitemia may be treated by administering doses of a pyrimidine analogue adequate, particularly in combination with the host's own defense systems (e.g., immune system), to inhibit the proliferation of the parasites, but insufficient to be toxic to the host's own cells (see Example 8, FIGS. 4A and 4B).

Several types of in vitro experiments can be used to screen compositions for effectiveness in practicing this invention:

1. Effects on parasite viability of orotate analogues alone or in combination with normal pyrimidine bases or nucleosides, or on the uptake of radioactive precursors of nucleic acid biosynthesis, e.g., [G-3-H]-hypoxanthine, can be tested on cultures of Plasmodium parasites, maintained according to Trager, et al. [Trager, W., et al., Science, 193:673–5 (1976)] and Haynes, et al. [Haynes, J. D., et al., Nature, 263:767–9 (1976)]. The in vitro anti-malarial activity of orotate analogues can be determined side-by-side with established anti-malarial drugs such as chloroquine. Different clones of Plasmodium can also be used as test malaria parasites, e.g., chloroquine-sensitive D6 clone from Sierra Leone and a chloroquine-resistant W2 clone from Indochina [Oduola, A. M. J., et al., Exp. Parasitol., 66:86–95 (1988)].

2. Effects of orotate analogues on cell viability and the ability to synthesize nucleic acids from radioactive precursors, and the rescuing effects of normal pyrimidine bases or nucleosides or amino acid derivatives such as histidinol, can be tested in human-derived tissue culture cell lines. Human HT-1080 human sarcoma cells [Rusheed, S., et al., Cancer, 33:1027–30 (1974)], human diploid IMR-90 cells [Nichols, W. W., et al., Science, 196:60–3 (1977)], human cervical sarcoma HeLa S3 cells [Puck, T. T., et al., J. Exp. Med., 103:273–84 (1956)], HL-60 human myeloid leukemia cells [Collins, S. J., et al., Nature, 270:347–9 (1977)], and mouse leukemia L-1210 cells [Moore, G. E., J. Nat. Cancer Inst., 36:405–21 (1966)] are particularly suitable for screening purposes, but those skilled in the art will know of other mammalian cell lines suitable for carrying out such screening tests. The growth medium most suitable for each cell line can be determined by reference to the publications cited above: briefly, HT-1080 cells are maintained in Eagle's Minimal Essential Medium (EMEM) supplemented with 5% fetal bovine serum (FBS) and 2 mM L-glutamine; IMR-90 cells are grown in EMEM supplemented with 10% FBS, 10 mM Hepes buffer, 0.21% $NaHCO_3$, and 2 mM L-glutamine. HeLA S3 cells are grown in EMEM plus 5% FBS, 20 mM Hepes, 0.21% $NaHCO_3$ and 2 mM L-glutamine. HL-60 cells are grown in EMEM plus 10% FBS, 15 mM Hepes, 0.21% $NaHCO_3$, 2 mM L-glutamine, and 1 mM sodium pyruvate. L-1210 cells are maintained in Dulbecco's medium [Stern, A. M., et al., *Cancer Res.*, 44:5614–8 (1954)].

Toxicity of pyrimidine analogues to cultured human cells is determined as follows. Mammalian cells are seeded into culture plate wells, and growth medium is added. The following day, fresh culture medium containing the appropriate pyrimidine analogues is added to the wells, and the plates incubated for a period of time and at a temperature appropriate to the cell line and the experimental requirements. Thereafter, the number of cells in each well is determined. Cells that attach to culture plates (e.g., HT-1080, IMR-90, HeLA S3 cells) are dislodged by trypsinization in the presence of a heavy metal chelator, e.g., EDTA, isolated by centrifugation at low speed (e.g., 300×g), washed with salt buffer (e.g., phosphate-buffered saline, PBS), and viability determined by exclusion of a vital stain, such as trypan blue. Cells that grow in suspension (e.g., HL-60 and L-1210 cells) are transferred to centrifuge tubes, pelleted at low speed, washed, and the viability determined as above. It is convenient to express susceptibility of cells by an $IC_{50}$ concentration, that is, the concentration of drug that kills 50% of the cells.

3. Effects of pyrimidine analogues alone or in combination with normal pyrimidine bases or nucleosides or with amino acid derivatives can be tested in malaria parasite-infected erythrocytes. Varying concentrations of pyrimidine analogues in culture medium are added to individual wells of microtitre plates [Desjardins, R. E. et al., *Antimicrob. Agents Chemotherap.*, 16:710–18 (1979)]. Parasitemic erythrocytes in culture medium are added to each well. Plates are incubated at suitable temperatures, e.g., about 37° C., for a suitable period, e.g., from about 1 hour to about 72 hours, under an atmosphere containing both $CO_2$ and $O_2$. Finally, a tracer concentration of a radioactive precursor of nucleic acid synthesis, e.g., [$G-^3H$]-hypoxanthine, is added to each well, and the incorporation of the precursor into nucleic acids determined according to Desjardin, et al. 1979 supra. As an alternative to adding a radioactive precursor of nucleic acid biosynthesis, the end point for determining the effects of added drugs can be the incorporation of a radioactive amino acid, e.g., [$U-^{14}C$]-isoleucine, into parasite protein.

Additionally, parasite-infected and treated erythrocytes can be smeared on microscope slides, stained with, e.g., Giemsa stain, and the ratio of infected to non-infected erythrocytes determined.

Several types of in vivo experiments in intact vertebrates can be used to test the effectiveness in vivo of the anti-malarial compositions of this invention. In one in vivo test system, dosage regimens for pyrimidine analogues are estimated by determining the pharmacokinetics of the drugs. Normal and malaria parasite-infected animals (preferably mice, but other rodents can be used) are injected once (preferably intraperitoneally, but subcutaneous or intravenous administration is also suitable) with the drug at various doses, e.g, from 0 to about 10 mg/kg body weight, preferably from about 0.2 to about 5 mg/kg body weight. At various time points (preferably from about 3 to about 180 minutes), blood samples are drawn from the animals and the amount of the drug in the plasma fraction determined as described in Example 7 below. The concentration of drug is plotted as a function of time for each drug dosage. From this data three important items of information are determined: (a) the time of peak plasma drug concentration at each dosage; (b) the half-life (t½) of the drug in the circulation at each dosage; and (c) drug dosages and frequency of administration of the drug that would maintain a therapeutically-useful concentration of the drug in the patient's circulation for a suitable length of time.

A second in vivo test system can be used to determine if repeated administration of the pyrimidine analogue would have safe anti-malarial activity. In this test system, groups of animals are infected with malaria parasites. At a time when blood parasitemia is reached, the animals are injected with saline alone (control) or with various concentrations of one or more pyrimidine analogues alone or together with one or more rescuing pyrimidine bases or nucleosides at a single concentration, at intervals, over a period of several days. In order to determine the prophylactic effectiveness of the rescuing pyrimidine base or nucleoside, the animals are pretreated with such a base or nucleoside prior to the administration of the pyrimidine analogue. Anti-malarial activity of the treatments is estimated by determining blood parasitemia on the animals at appropriate times. The safety of the treatments is estimated by monitoring animals for weight loss and diarrhea, as these are early symptoms of pyrimidine analogue toxicity [Houghton, J. A., et al., *Cancer Res.*, 39:2406–13 (1979)].

The composition of this invention can be administered in any appropriate pharmacological vehicle for oral or parenteral administration. They can be administered by any means that provides prophylaxis and/or therapy to humans and other vertebrates. The dosage administered will be dependent upon the age, health and body weight of the recipient, kind of concurrent treatment, if any, and the nature of the effect desired.

The composition can be employed in dosage forms such as tablets, capsules, powder packets, or liquid solutions, suspensions or elixirs for oral administration, and sterile liquid for formulations such as solutions or suspensions for parenteral use. Materials such as anti-oxidants, viscosity stabilizers and the like may be added, if necessary, to such dosage forms.

In order that those skilled in the art can more-fully understand this invention, the following examples are set forth. These examples are given solely for purposes of illustration, and should not be considered as expressing limitations unless so set forth in the appended claims.

EXAMPLE 1

Anti-Malarial Activity of 5-Fluoro-pyrimidines Against *P. falciparum*

Fluoropyrimidines, dispersed in 25 μl of culture medium, were added to individual wells of a 96-well microtitre plate. Human erythrocytes with 0.25–0.5% parasitemia (clone W2 of *P. falciparum*) were added to each well in 200 μl of culture medium to give a final hematocrit of 1.5%. Plates were incubated at 37° C. for 48 hours under 5% $CO_2$-5% $O_2$. Finally, the incorporation of 0.5 μCi of [$G-^3H$]hypoxanthine (1 Ci/mmol) into nucleic acids in each well was determined; this served as a measure of parasite proliferation. Control wells incorporated 11,200 cpm of $^3$H into precipitable material. As shown in FIG. 1A, 5-fluoro-orotate showed potent antimalarial activity against the Indochina clone of $P.$ $falciparum$ ($IC_{50}$=6.0 nM); 5-fluoro-uracil ($IC_{50}$=12 $\mu$M), 5-fluoro-uridine ($IC_{50}$=32 $\mu$M) and 5-fluoro-2'-deoxyuridine ($IC_{50}$=100 $\mu$M) were much less effective.

EXAMPLE 2

Comparison of the In-vitro Anti-Malarial Activity of 5-Fluoro-Orotate With That of Conventional Anti-Malarial Drugs Using $P.$ $falciparum$ Clones Using the experimental system described in Example 1 above, the anti-malarial activity of 5-fluoro-orotate against the Indochina and Sierra Leone clones of $P.$ $falciparum$ was compared to that of chloroquine, quinine, pyrimethamine and sulfadoxine.

As shown in Table 1 below, 5-fluoro-orotate was from about 14 to over 4,000 times more effective against the Indochina W2 clone (chloroquine-resistant) than were conventional anti-malarial drugs. Against the Sierra Leone D6 clone of $P.$ $falciparum$ (chloroquine-sensitive strain), 5-fluoro-orotate was a more-effective anti-malarial than all but the highly toxic (to mammalian cells as well) pyrimethamine.

TABLE 1

Comparison of Inhibitory Activity of 5-Fluoro-orotate and Conventional Anti-Malarial Drugs Against Plasmodium falciparum Clones

| Drug | Indochina Clone | | Sierra Leone Clone | |
| --- | --- | --- | --- | --- |
| | $IC_{50}$* (nM) | Molar Index | $IC_{50}$* (nM) | Molar Index[+] |
| 5-Fluoroorotate | 6.0 ± 1.7 | 1 | 5.8 ± 3.1 | 1.0 |
| Chloroquine | 127 ± 23 | 21 | 9.0 ± 1.7 | 1.6 |
| Quinine | 83 ± 5 | 14 | 12.7 ± 6.8 | 2.2 |
| Pyrimethamine | 111 ± 29 | 19 | 0.24 ± 0.16 | 0.04 |
| Sulfadoxine | 25593 ± 7077 | 4344 | 76.2 ± 13.2 | 13.5 |

*Numerical values show mean ± S.D. of five independent drug response curves.
*Molar indices illustrate in vitro equimolar activities of 5-fluoroorotate relative to conventional drugs. For example, 5-fluoroorotate is 21 times more active than chloroquine against the multi-drug-resistant Indochina clone and 1.6 times more active than chloroquine against the chloroquine-sensitive Sierra Leone clone.

EXAMPLE 3

Toxicity of 5-Fluoro-Orotate Against $P.$ $falciparum$ Determined by Three In Vitro Test Methods The chloroquine-sensitive Sierra Leone clone of $P.$ $falciparum$ was cultured in erythrocytes as in Example 1 above. In one method of determining the toxicity of 5-fluoro-orotate, [G-$^3$H]-hypoxanthine uptake was used as an indicator of parasite proliferation, according to the procedure of Example 1 above. In a second method, the increase in parasitemia was determined directly by smearing infected erythrocytes on microscope slides, staining with Giemsa stain, and determining the ratio of infected to non-infected erythrocytes. In a third method, parasite-infected erythrocytes were incubated with [U-$^{14}$C]-isoleucine (0.5 $\mu$Ci; 0.33 Ci/mmol), and the amount of radioactivity incorporated into precipitable proteins determined.

TABLE 2

| Test Method | $IC_{50}$, nM |
| --- | --- |
| Hypoxanthine uptake | 2.2 |
| Light microscopy | 2.5 |
| Isoleucine uptake | 4.7 |

Table 2 above shows that all three test methods yielded similar $IC_{50}$ values. Therefore, each of these three tests is a valid measure of 5-fluoro-orotate toxicity to malarial parasites in cultures.

EXAMPLE 4

Effects of Pyrimidine Analogues on Mammalian Cells

Proliferation of human fibrosarcoma cells (HT-1080) was determined directly by measuring the number of viable cells per culture well.

HT-1080 cells were seeded into 6-well culture plates at a density of 50,000 cells per 9.6 cm$^2$ well. Each well contained 2.5 ml of growth medium. The following day, fresh culture medium containing the appropriate fluoropyrimidine was added to the wells, and the plates were incubated at 37° C. for 48 hours in a 5% $CO_2$ incubator. Thereafter, plates were washed with $Ca^{2+}$—$Mg^{2+}$-free phosphate-buffered saline (PBS-CMF, 136 mM NaCl, 2.7 mM KCl, 8 mM $Na_2HPO_4$, 1.5 mM $KH_2PO_4$), and then treated with 1 ml of 0.05% trypsin and 0.02% EDTA in PBS-CMF. After 1 minute, the detached cells were suspended in 1.0 ml of EMEM and collected by centrifugation at 300×g for 3 minutes. Cell pellets were suspended in 1 ml of PBS-CMF, and a 0.5 ml portion of this suspension was mixed with 0.4 ml of PBS-CMF and 0.1 ml of Trypan blue solution (0.5% of the dye in 0.85% saline). The concentrations of viable cells were determined in a hemocytometer.

As shown FIG. 1B, it required about 10 $\mu$M of 5-fluoro-orotate to cause a 50% inhibition of these human cells as compared to 6 nM to achieve the same results with $P.$ $falciparum$ (FIG. 1A), indicating that these human cells are less sensitive to the analogue than are the parasites. The HT-1080 mammalian cell line was less vulnerable to 5-fluoro-orotate than to the commonly-used anti-cancer drugs, 5-fluoro-uracil ($IC_{50}$=2 $\mu$M), 5-fluoro-uridine ($IC_{50}$=30 nM) and 5-fluoro-2'-deoxy-uridine ($IC_{50}$=10 nM) (FIG. 1B), indicating that orotate analogues are preferable to uracil or uridine analogues in the prophylactic and therapeutic compositions of the invention.

EXAMPLE 5

Comparison of Inhibitory Activity of 5-Fluoro-Orotate Against Different Mammalian Cell Lines— Rescue Effect of Uridine Using the test system of Example 4 above, the toxicity of 5-fluoro-orotate was tested against a battery of four human cell lines and a rapidly dividing mouse cell line. As shown in Table 3, even though the $IC_{50}$ values ranged between 0.9 and 10 $\mu$M, none of the mammalian cell lines approached the vulnerability of malarial parasites ($IC_{50}$=6 nM, FIG. 1A) to this pyrimidine analogue.

In five mammalian cell lines, added 1 mM uridine reduced the inhibitory effect of 5-fluoro-orotate on cells (Table 3, right column). Depending on the cell line, the $IC_{50}$ values for 5-fluoro-orotate were 2 to 5 times higher in the presence of 1 mM uridine than in its absence. These data substantiate the inventive concept that uridine can be used in a prophylactic or therapeutic anti-malarial composition to rescue the host vertebrate from the toxic effects of the pyrimidine analogue, 5-fluoro-orotate.

TABLE 3

Comparison of Inhibitory Activity of 5-Fluoro-Orotate Against Different Mammalian Cell Lines in the Absence and Presence of Uridine

| Cell Line | Cell Line | $IC_{50}$ ($\mu M$) | |
| --- | --- | --- | --- |
| | | Without Uridine | With 1 mM Uridine |
| HT-1080 | Human Fibrosarcoma | 10 | 50 |
| IMR-90 | Human Lung Fibroblast | 1.1 | 2.2 |
| HeLa S3 | Human Cervix Epithelioid Carcinoma | 2.0 | 3.5 |
| HL-60 | Human Promyelocytic Leukemia | 0.9 | 4.5 |
| L-1210 | Mouse Lymphocytic Leukemia | 2.8 | 5.0 |

EXAMPLE 6

Effects of Uridine on the In Vitro Cytotoxicity of 5-Fluoro-Orotate

As in Examples 1 and 4 above, malaria parasites (Indochina clone W-2 of *P. falciparum*) and human HT-1080 cells were grown for 48 hours with varying concentrations of 5-fluoro-orotate in the absence and presence of 1 mM uridine.

As shown in FIG. 2, the cytotoxicity of 5-fluoro-orotate to human HT-1080 cells was decreased 5-fold by simultaneous administration of 1 mM uridine. In contrast, uridine had no effect on the cytotoxicity of 5-fluoro-orotate towards malarial parasites.

EXAMPLE 7

Pharmacokinetics of 5-Fluoro-orotate in Mice

Pairs of Swiss white mice (Charles River Labs, Mass.) were injected intraperitoneally with 200 $\mu$l of [2-$^{14}$C]-5-fluoro-orotate in saline (55 $\mu$Ci/$\mu$mol). Single injections of the drug were made at dosages of 0.2, 1 and 5 mg/kg body weight. At time points ranging from about 3 to about 180 minutes, two 200 $\mu$l blood samples were drawn from the tail veins of the mice, and the amount of 5-fluoro-orotate present in the plasma determined, as described below.

Blood samples were immediately diluted in 100 $\mu$l of cold saline, and centrifuged in a desk top Eppendorf centrifuge for 1 minute to separate the plasma fraction from blood cells. Cell pellets were washed with 100 $\mu$l of saline, centrifuged, and the supernatant fractions mixed with plasma fractions. In order to determine the 5-fluoro-orotate concentrations of the diluted plasma fractions, the radioactive content of half the samples was determined by liquid scintillation spectrometry. The remaining samples were chromatographed on a Pharmacia FPLC system using a Mono Q anion-exchange column. Ninety minutes after 5-fluoro-orotate injection, the radioactive counts from the plasma fraction co-migrated with a non-radioactive 5-fluoro-orotate standard confirming that radioactivity in the plasma fraction was due to 5-fluoro-orotate and not some secondary metabolite of the experimental drug.

Figure 3:
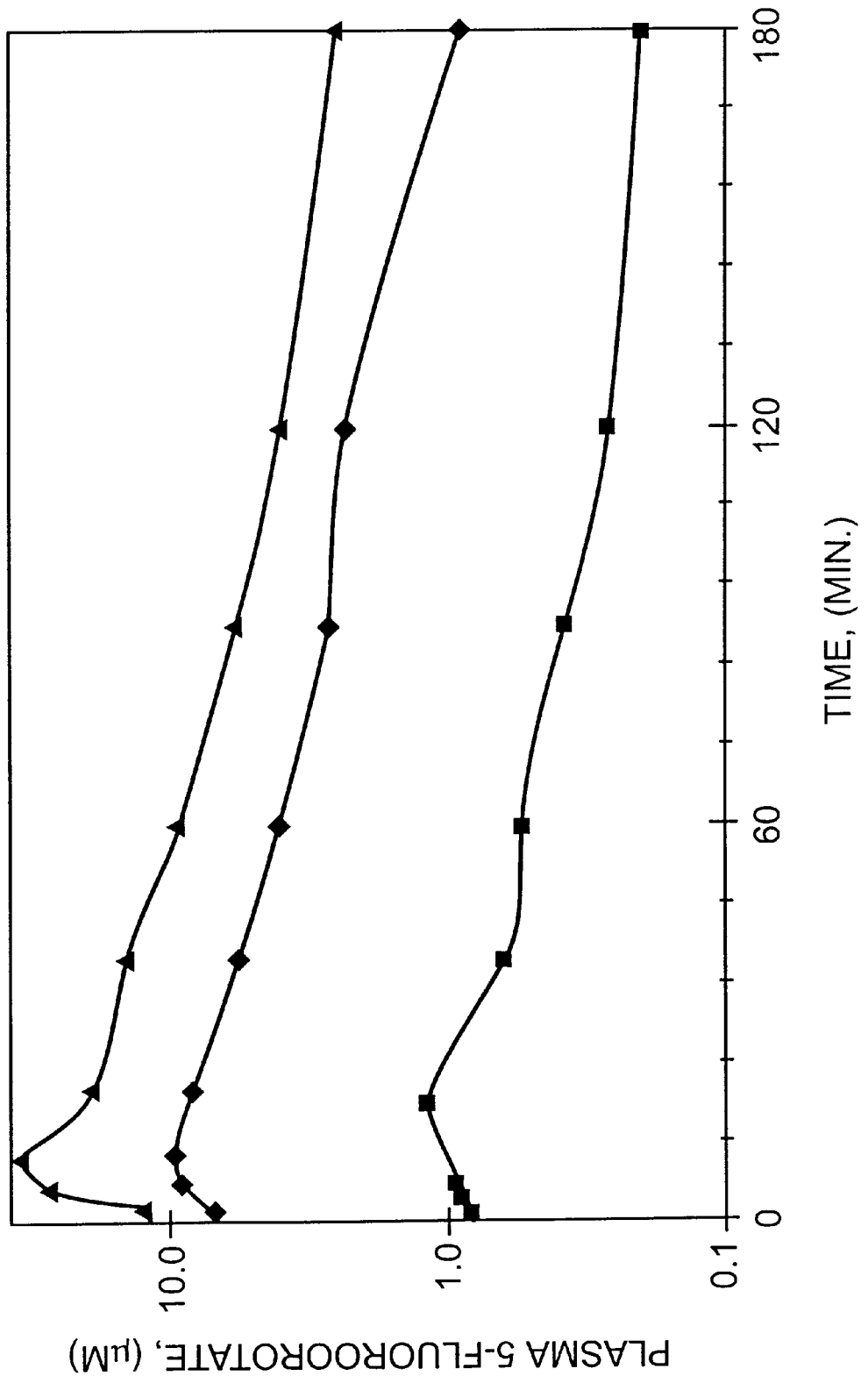
FIG. 3 illustrates time-dependant changes in plasma 5-fluoroorotate concentration following single intraperitoneal injections of 5-fluoro-orotate at 0.2 mg/kg (■), 1 mg/kg (♦), or 5 mg/kg (▲). Two mice were used at each dosage level. At each time point, duplicate 200 μl samples of blood were drawn and analyzed for 5-fluoro-orotate concentration.

As shown in FIG. 3, at all dosages tested, plasma 5-fluoro-orotate concentrations peaked within about 20 minutes. Thereafter, the drug was lost from the circulation with a t½ of about 90 minutes. With a single dose of 5 mg/kg, plasma concentrations of the drug reached values as high as about 30 $\mu$M, but rapidly dropped to below 10 $\mu$M. At a dose of 0.2 mg/kg, the drug concentration did not exceed about 2 $\mu$M, and dropped below 0.5 $\mu$M within 60 minutes. Less than 10% of the total circulating radioactivity was associated with blood cells. The pharmacokinetic profile of plasma 5-fluoro-orotate in mice infected with *P. yoelii* (10% parasitemia), tested at 1 mg/kg, was essentially the same as that of uninfected mice.

These data suggest that a dose of about 0.2 to about 5 mg/kg administered every 4 hours would maintain plasma 5-fluoro-orotate at about 0.1 to about 1 $\mu$M under in vivo conditions. As shown in Example 1 above, *P. falciparum* exposed to 0.1 to 1 $\mu$M 5-fluoro-orotate for 48 hours ceased to incorporate hypoxanthine and ceased to proliferate. In addition, as shown in Example 4 above, these concentrations of the drug were not toxic to rapidly dividing mammalian cells in culture.

EXAMPLE 8

In Vivo Effects of Therapeutic Compositions on Parasite-Infectivity and Host Toxicity in Mice Swiss white mice (25–30 g) were divided into groups of five. On day 0, each mouse was infected by intraperitoneal injection of $10^5$ erythrocytic forms of *P. yoelii*. Starting on day 3, when the blood parasitemia had reached between 5 and 12%, the mice were injected intraperitoneally every 4 hours for three consecutive days with 200 $\mu$l of various formulations. In experiment 1, three groups of mice received 0.2, 1, or 5 mg/kg of 5-fluoro-orotate per injection, respectively. An accompanying control group received saline. In experiment 2, three groups of mice received 0.2, 1, or 5 mg/kg of 5-fluoro-orotate plus 800 mg/kg of uridine in a 200 $\mu$l saline formulation. An accompanying control group received 800 mg/kg of uridine alone. In experiment 2, mice were pretreated with one injection of 800 mg/kg of uridine two hours before receiving the first injection of 5-fluoro-orotate. Additionally, even though treatment with the pyrimidine analogue stopped on day 6, these mice continued to receive 1500 mg/kg of uridine, three times a day, for three additional days (i.e., up to day 9).

Figure 4A:
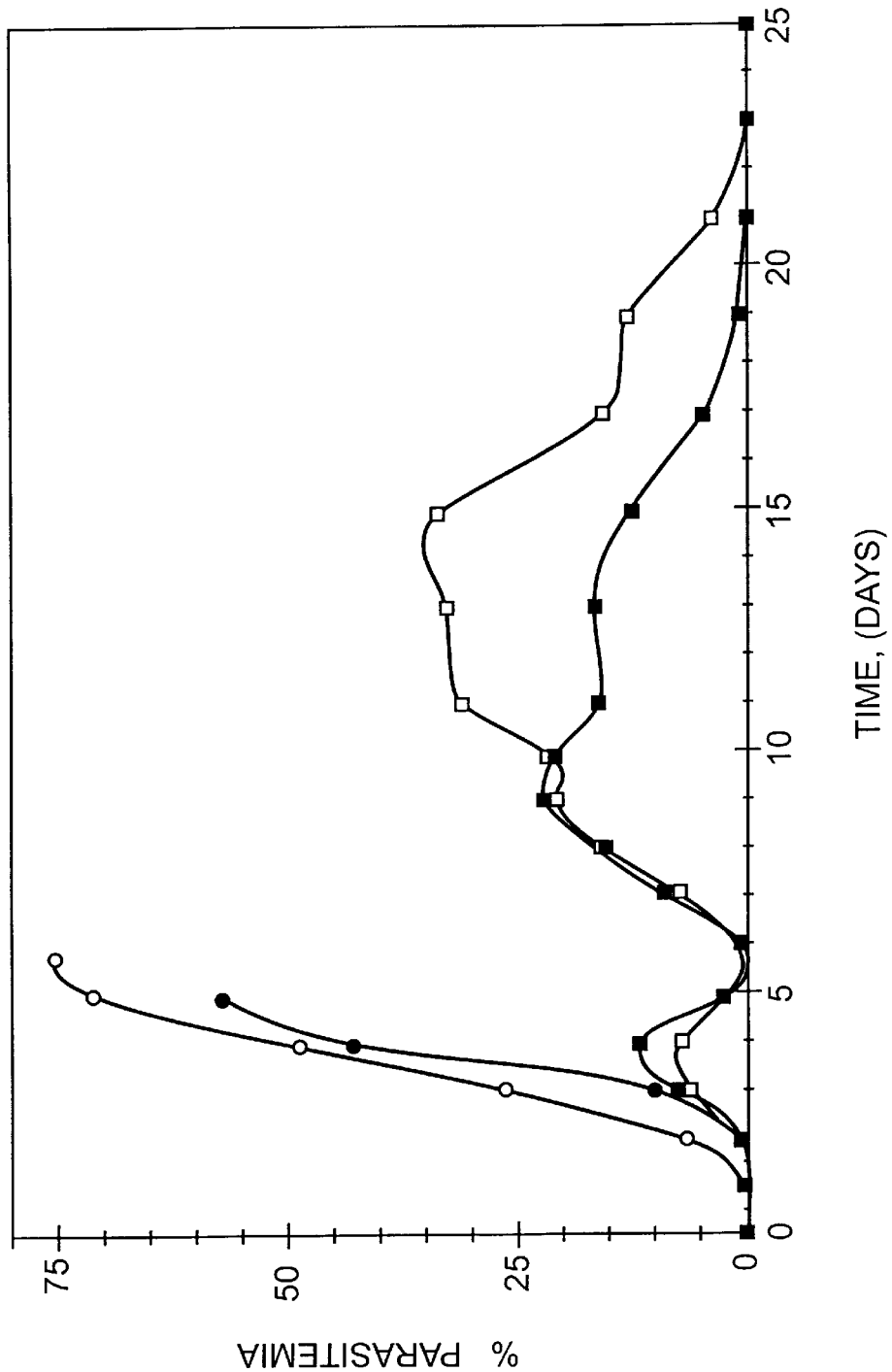
FIG. 4 illustrates the effect of 5-fluoro-orotate treatment on blood parasitemia. Mice infected with *P. yoelii* on day 0 in experiments 1 and 2 were treated with (A) 0.2 mg/kg 5-fluoro-orotate, (B) 1 mg/kg, or (C) 5 mg/kg every 4 hours for three days. Control mice (○, ●, respectively), received no drug. Open symbols represent treatment without uridine (experiment 1: ○, □, ◇, △), and filled symbols represent animals also treated with uridine (experiment 2: ●, ■, ♦, ▲). Animals were treated with 5-fluoro-orotate on days 3 to 6. Animals were also treated with uridine in experiment 2 on days 3 to 9.
Figure 4B:
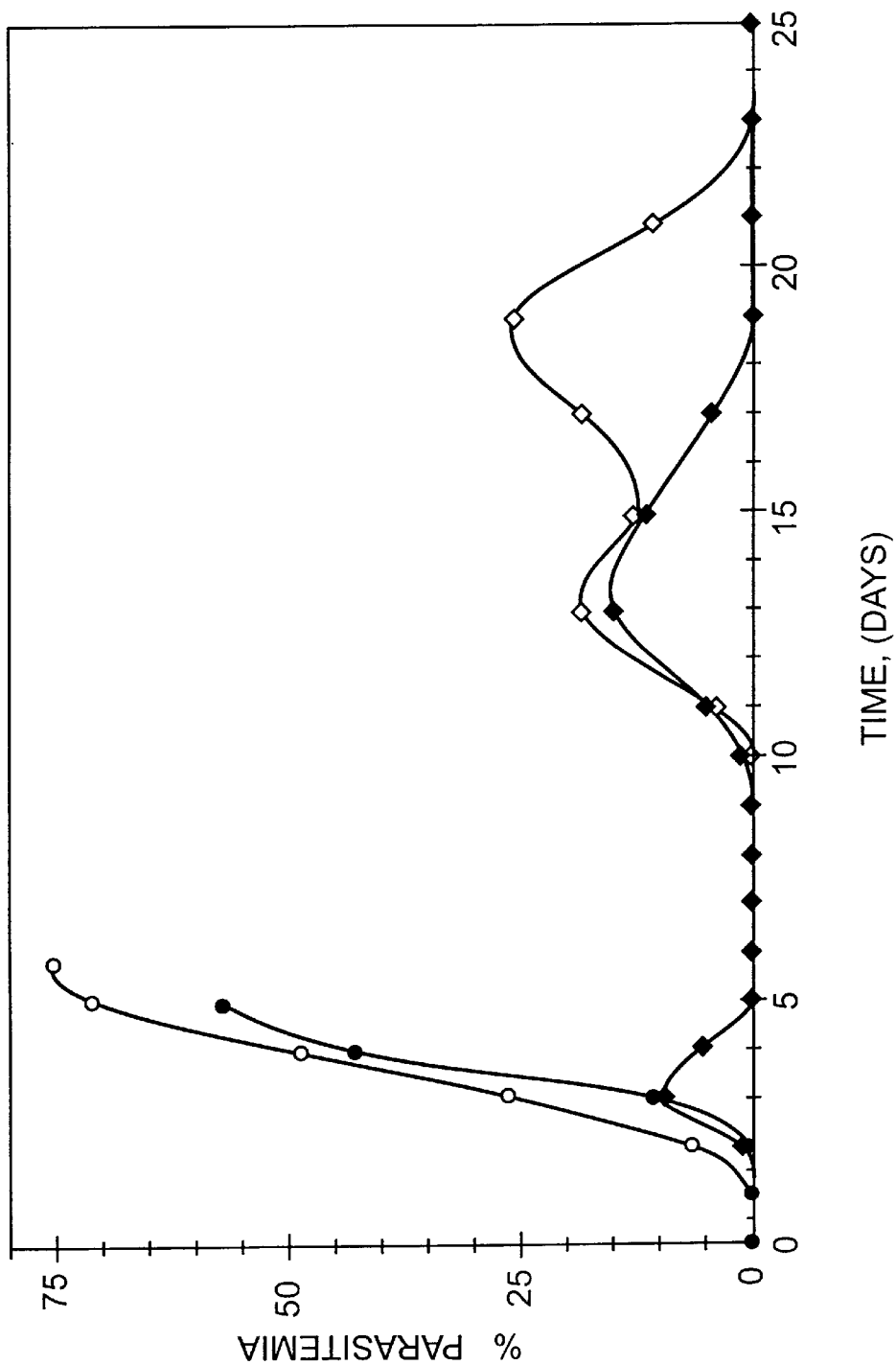
Figure 4C:
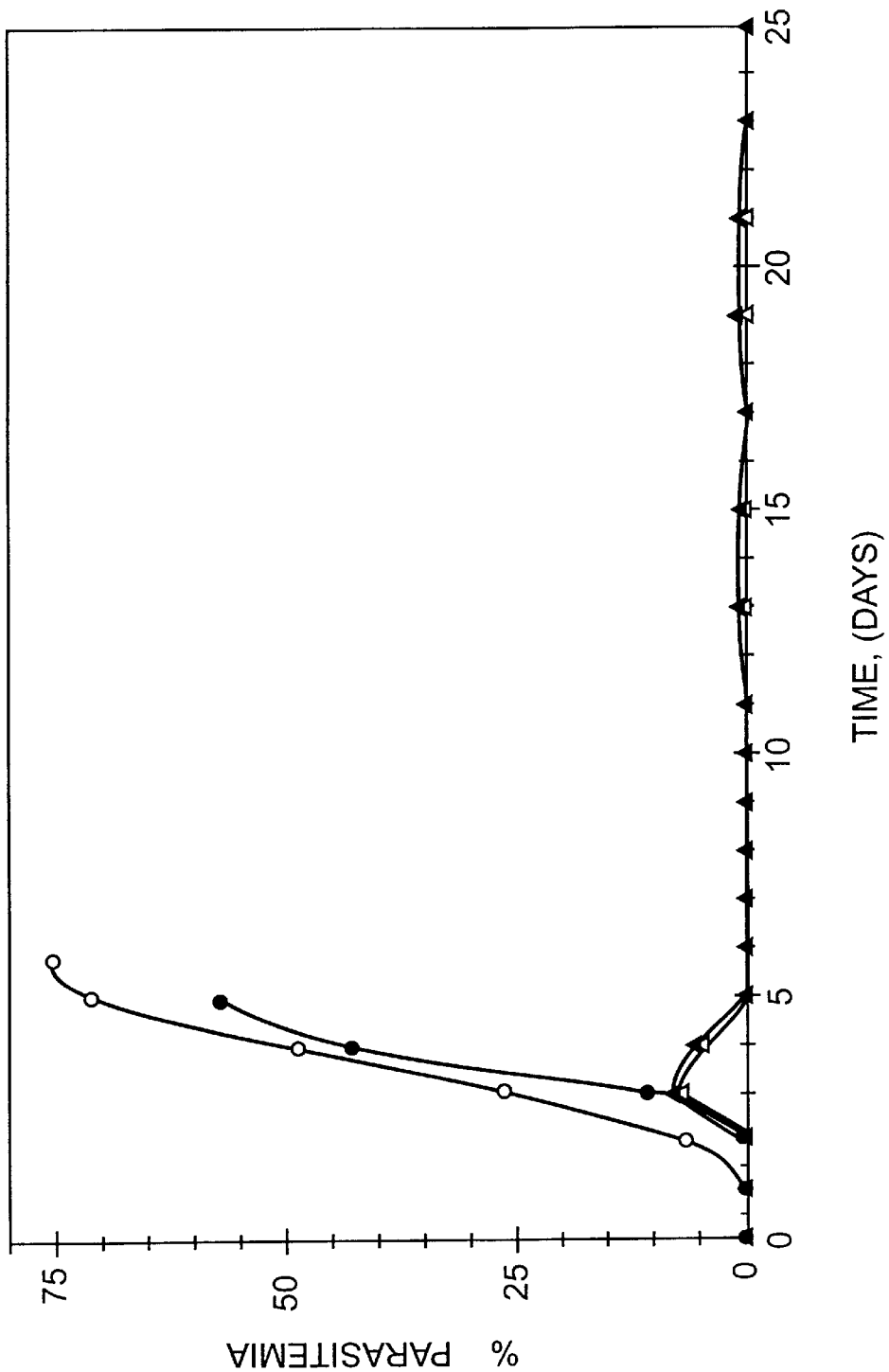

The results of these in vivo experiments showed that 5-fluoro-orotate exhibited a dose-dependent ability to suppress parasitemia in mice infected with the malaria parasite, *P. yoelii*. In experiments 1 and 2, mice not receiving 5-fluoro-orotate showed a rapid increase in parasitemia (FIGS. 4A–C). By day 6 after infection, parasitemia levels as high as 75% were seen in those mice that had not died of the infection. In contrast, every mouse treated with the pyrimidine analogue showed a rapid decrease in parasitemia between days 3 and 6 (FIGS. 4A–C).

Once treatment with 5-fluoro-orotate was stopped on day 6, mice that had been treated with the lowest dose, i.e., 0.2 mg/kg, showed a return of parasitemia within 24 hours (FIG. 4A). Similarly, mice treated with 1 mg/kg of the analogue also showed a recurrence of infection, although recurrence was delayed compared to the lower dosage (FIG. 4B). Such recurring parasitemias were seen at low doses of the 5-fluoro-orotate in experiments 1 and 2. Within a period of about 14 days, the second surge of parasitemia resolved itself without the need for additional treatment with the drug (FIGS. 4A and 4B), suggesting that the immune system of the mice was able to destroy parasites that had previously been weakened by the 5-fluoro-orotate.

A dose of 5 mg/kg of 5-fluoro-orotate completely prevented this second surge of parasitemia (FIG. 4C).

The anti-malarial activity of 5-fluoro-orotate was not compromised by the co-administration of uridine in experiment 2, in keeping with the in vitro results observed in Example 5 above.

Figure 5A:
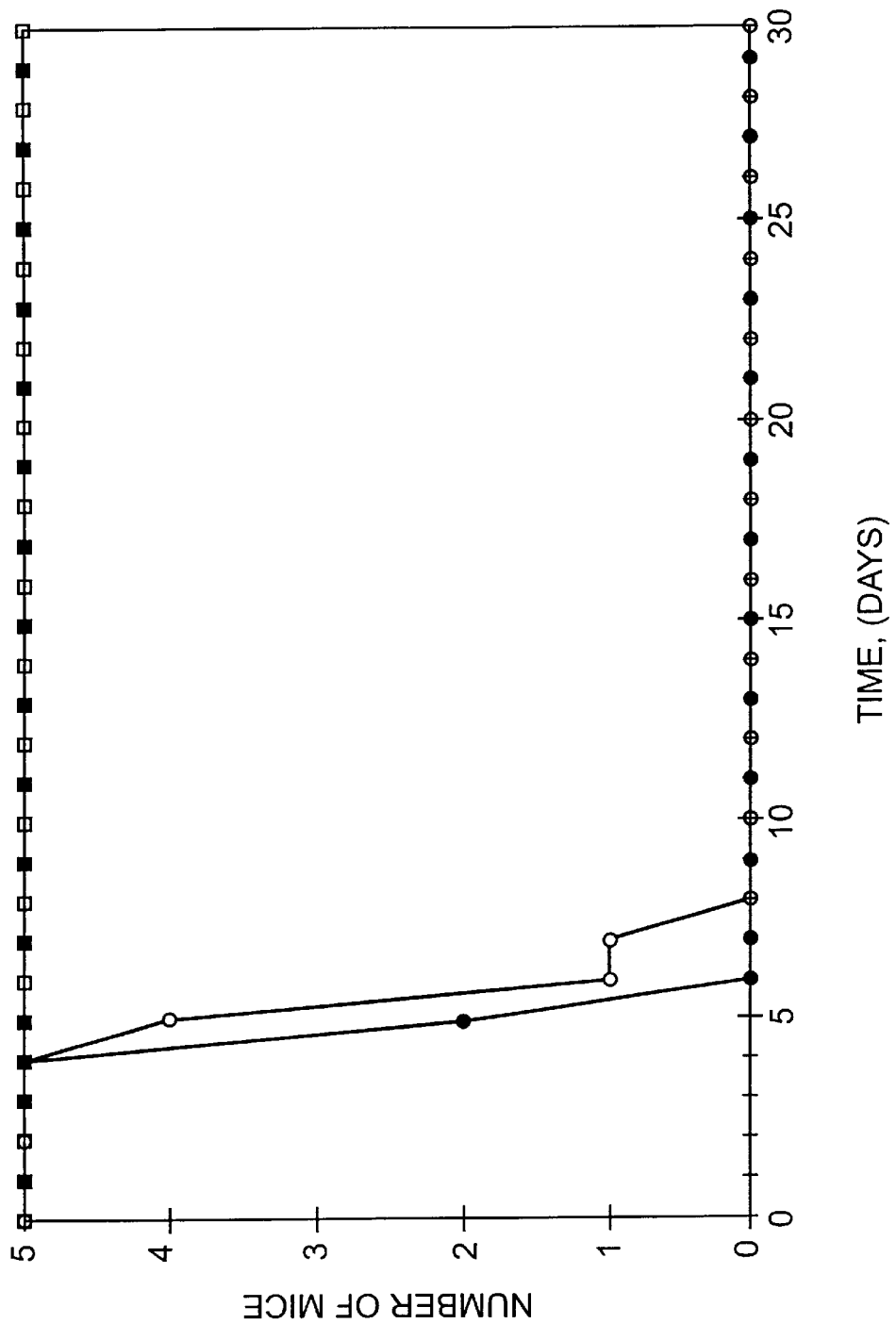
FIG. 5 illustrates the survival rate of mice infected with *P. yoelii* and treated with 5-fluoro-orotate, alone or in combination with uridine. Mice were treated with (A) 0.2 mg/kg 5-fluoro-orotate, (B) 1 mg/kg, or (C) 5 mg/kg. Control mice received no 5-fluoro-orotate (○, ●, respectively). Open symbols represent treatment without uridine (experiment 1: ○, □, ◇, △), and closed symbols represent animals also receiving uridine (experiment 2: ●, ■, ♦, ▲).
Figure 5B:
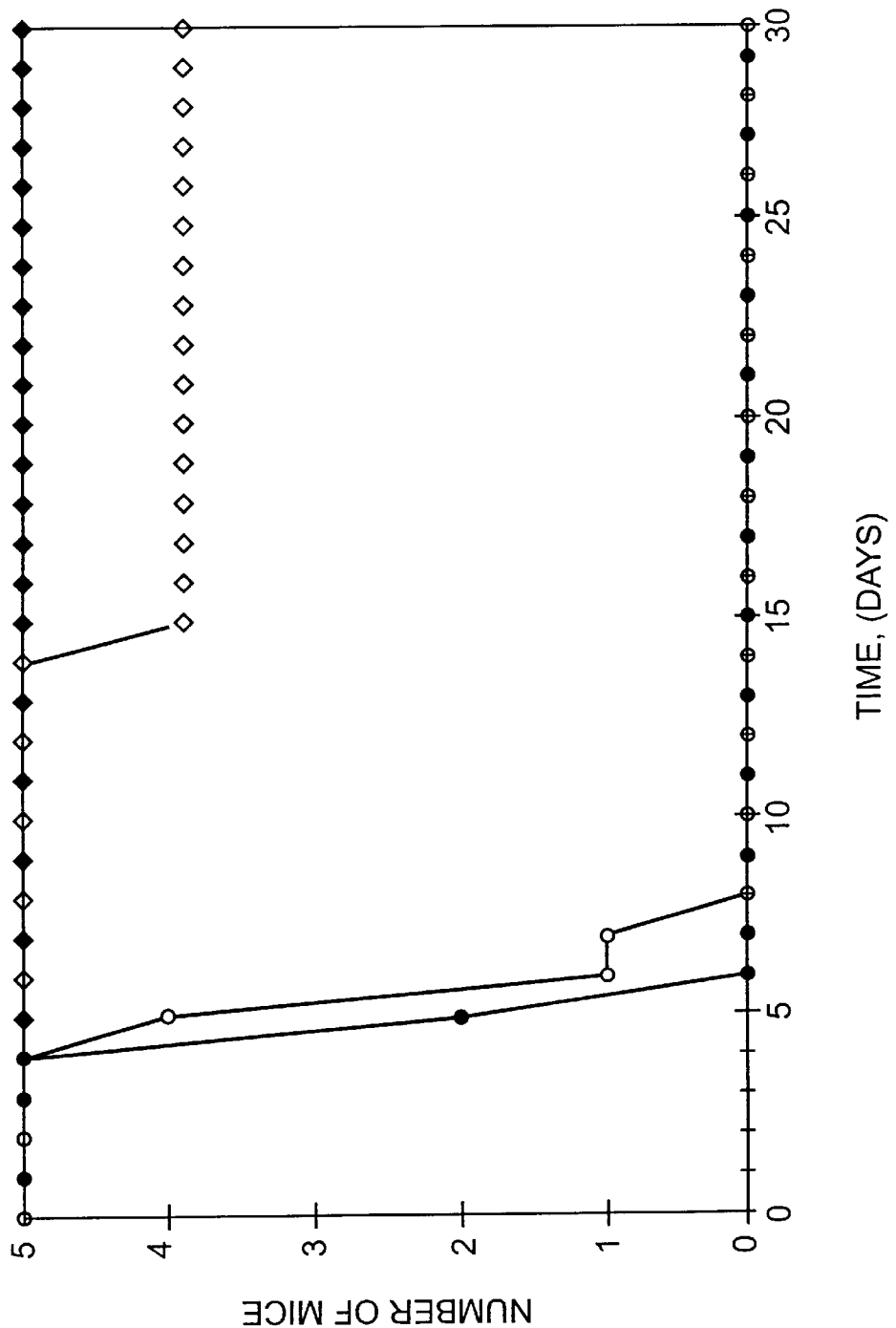
Figure 5C:
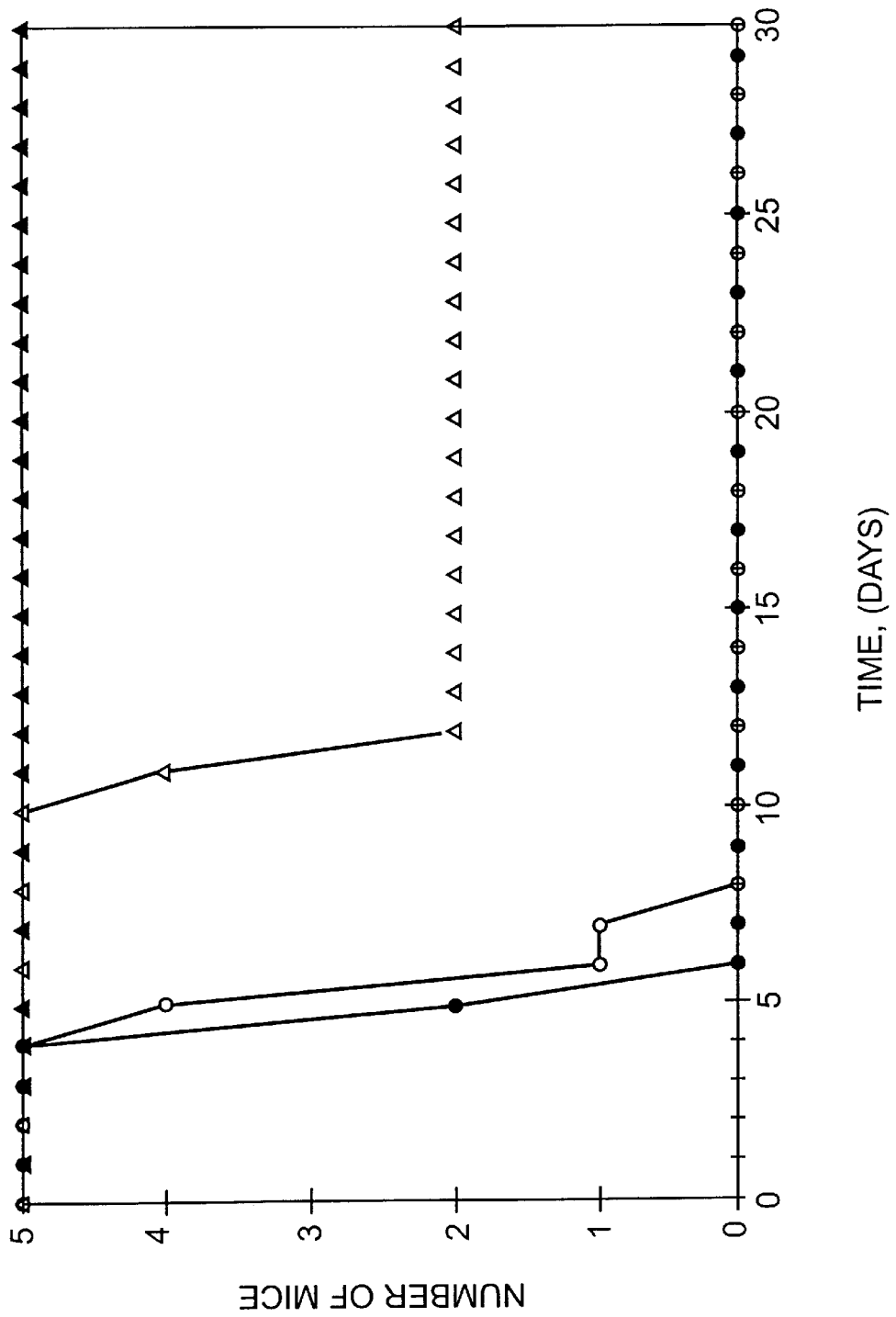

In experiment 1, mice that did not receive 5-fluoro-orotate all succumbed to *P. yoelii*, but none of the mice that received 0.2 mg/kg of the analogue perished (FIG. 5A). At higher doses, i.e., 1 and 5 mg/kg, of the analogue, there was a dose-dependent increase in mortality of mice not receiving uridine (FIGS. 5B and 5C, respectively). The mice that survived showed signs of diarrhea. The mice receiving 5 mg/kg of 5-fluoro-orotate did not die of malaria; no parasites were observed in blood just prior to death.

Figure 6:
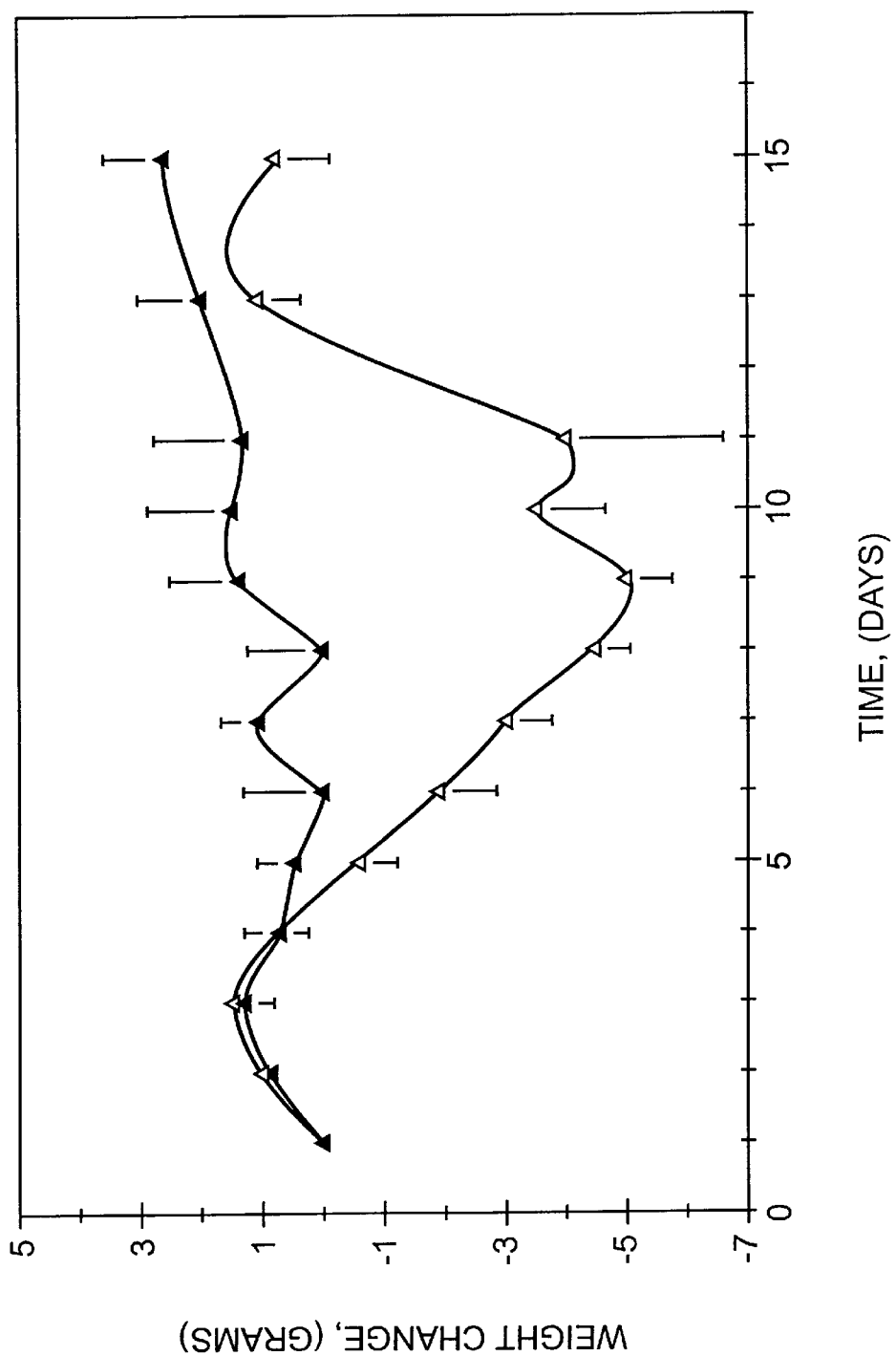
FIG. 6 illustrates the weight changes in mice receiving 5 mg/kg of 5-fluoro-orotate without (△) or with (▲) uridine. The pyrimidine analogue was administered on days 3 to 6. The pyrimidine nucleoside was given to mice in experiment 2 on days 3 to 9. Data points represent mean weights of mice that remained alive during the course of experiments 1 and 2 (see FIG. 5C). Error bars represent standard deviations from the mean.

Mice receiving uridine either before or along with 5-fluoro-orotate were cured of malaria without suffering from drug toxicity. In experiment 2, mice not receiving 5-fluoro-orotate all succumbed to *P. yoelii*, but no mouse receiving 0.2, 1- or 5 mg/kg of the analogue perished from the malaria. In addition, no mouse had diarrhea, and even at the highest drug dose (5 mg/kg), mice showed no weight loss (FIG. 6).

Mice that received 5-fluoro-orotate subsequent to infection by *P. yoelii* were considered cured by the following criteria. One, for periods as long as sixty days after initial infection, no parasites were detected in blood smears of any of the 5-fluoro-orotate-treated mice. In these studies, greater than 10,000 Wright's stain treated red blood cells were inspected under the microscope. Two, when $10^6$ erythrocytes from five different 5-fluoro-orotate-treated mice were injected intraperitoneally into five separate naive mice, no infections developed in the recipients. The treated mice were from the 0.2 mg/kg group, 60 days after the original infection. Three, when a standard innoculum of $10^6$ *P. yoelii* parasites was injected into the same five 5-fluoro-orotate-treated mice, a transient parasitemia of less than 0.05% was observed between days 2 and 4; after day 4, no parasites were observed in these challenged mice. This last experiment showed that these mice were not only cured, but protected from new infections.

In summary, the experiments of Example 8 demonstrate that mice infected with *P. yoelii* were (apparently permanently) cured of malaria by multiple doses of 5-fluoro-orotate. At low doses, the elimination of the malarial parasite may rely on the immune system. A higher dose of 5 mg/kg body weight every 4 hours, which is required for radical elimination of malarial parasites, was tolerated only when uridine was administered in combination with 5-fluoro-orotate. The host mammal readily tolerated even the highest dose of 5-fluoro-orotate when uridine was administered either before, during or after infection with Plasmodium. These in vivo results support prophylactic and therapeutic anti-malarial uses of the compositions of the invention.

The above disclosure of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

What is claimed is:

1. A method of controlling malaria-causing Plasmodium parasites in a living mammalian host infected with such parasites which comprises administering to said living mammalian host (1) an effective amount of a compound which blocks the de novo pathway for the biosynthesis of the pyrimidine nucleotides essential for RNA and DNA synthesis in said parasites, said compound being selected from the group consisting of 5-fluoro-orotic acid, esters and amides of the aforementioned orotic acid, O-acyl and N-acyl derivatives of the aforementioned orotic acid, and cis and trans-5,6-dihydro counterparts and (2) a member of the group consisting of uracil, uridine, cytosine, cytidine, thymine, deoxythymidine and deoxycytidine in amount sufficient to minimize toxic effects caused by administration of said compound to said host.

2. A method of controlling malaria-causing Plasmodium parasites in a living mammalian host infected with such parasites which comprises administering to said living mammalian host (1) an effective amount of a compound which blocks the de novo pathway for the biosynthesis of the pyrimidine nucleotides essential for RNA and DNA synthesis in said parasites, said compound being 5-fluoro-orotic acid, and (2) a member of the group consisting of uridine and doxythymidine in an amount sufficient to minimize toxic effects caused by administration of said compound to said host.

* * * * *